(12) United States Patent
Sumiya et al.

(10) Patent No.: US 10,349,829 B2
(45) Date of Patent: Jul. 16, 2019

(54) OPHTHALMIC IMAGING APPARATUS

(71) Applicant: CANON KABUSHIKI KAISHA, Tokyo (JP)

(72) Inventors: Toshiharu Sumiya, Hiratsuka (JP); Yasuhisa Inao, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/476,596

(22) Filed: Mar. 31, 2017

(65) Prior Publication Data

US 2017/0311795 A1 Nov. 2, 2017

(30) Foreign Application Priority Data

Apr. 28, 2016 (JP) .................................. 2016-091609

(51) Int. Cl.
| | |
|---|---|
| *A61B 3/10* | (2006.01) |
| *A61B 3/00* | (2006.01) |
| *A61B 3/14* | (2006.01) |
| *F21V 8/00* | (2006.01) |
| *G02F 1/225* | (2006.01) |
| *G01B 9/02* | (2006.01) |
| *G02F 1/21* | (2006.01) |

(52) U.S. Cl.
CPC ............ *A61B 3/102* (2013.01); *A61B 3/0025* (2013.01); *A61B 3/14* (2013.01); *G01B 9/02004* (2013.01); *G01B 9/02091* (2013.01); *G02B 6/0008* (2013.01); *G02F 1/2252* (2013.01); *G02F 2001/212* (2013.01)

(58) Field of Classification Search
CPC ........... A61B 3/14; A61B 3/0025; A61B 3/12; A61B 3/102; A61B 3/0058

USPC .................................................. 351/200–246
See application file for complete search history.

(56) References Cited

U.S. PATENT DOCUMENTS

| | | | |
|---|---|---|---|
| 2011/0102741 A1* | 5/2011 | Hirose | ...................... A61B 3/14 351/206 |
| 2012/0249953 A1* | 10/2012 | Ono | ...................... A61B 3/102 351/206 |
| 2016/0320564 A1 | 11/2016 | Murashima | |

FOREIGN PATENT DOCUMENTS

| | | |
|---|---|---|
| JP | 7-281054 A | 10/1995 |
| JP | 2008191369 A | 8/2008 |
| JP | 2013156229 A | 8/2013 |

* cited by examiner

*Primary Examiner* — Mohammed A Hasan
(74) *Attorney, Agent, or Firm* — Canon U.S.A., Inc. IP Division

(57) ABSTRACT

An ophthalmic imaging apparatus that captures a tomographic image of an subject's eye based on light obtained by combining a return light with a reference light, the return light being from the subject's eye when irradiated with a measurement light, the reference light corresponding to the measurement light includes a first optical fiber disposed in an optical path of the reference light and including a light guide portion for guiding the reference light, and a second optical fiber disposed in an optical path of the measurement light and including a light guide portion for guiding the measurement light, wherein a diameter of each of the light guide portions of ejection ends of the first optical fiber and the second optical fiber is larger than a diameter of a light guide portion in a position different from a position of each of the ejection ends.

29 Claims, 8 Drawing Sheets

OPHTHALMIC IMAGING APPARATUS

BACKGROUND OF THE INVENTION

Field of the Invention

The present invention relates to an ophthalmic imaging apparatus that captures a tomographic image of a subject's eye by using optical coherence tomography.

Description of the Related Art

An optical coherence tomography (OCT) has been practically used as a method for obtaining a tomographic image of a measurement object such as a living body in a nondestructive manner and a noninvasive manner. Particularly, the OCT is widely used in the field of ophthalmology to obtain a tomographic image of a retina of a fundus of a subject's eye for ophthalmic diagnosis on the retina.

According to the OCT, measurement light reflected from a measurement object and reference light reflected from a reference mirror interfere with each other, and time dependency or wavenumber dependency of intensity of the interference light is analyzed to obtain a tomographic image. A swept source optical coherence tomography (SS-OCT) apparatus with a wavelength-sweeping light source capable of changing an oscillation wavelength is known as such an optical coherence tomographic image obtaining apparatus.

Conventionally, fix pattern noise (FPN) in a tomographic image is removed by noise reduction processing (e.g., DC subtraction), and the resultant tomographic image is displayed. However, even if the conventional noise reduction processing is performed, noise appears in a tomographic image that is obtained by the SS-OCT due to complications of control of a wavelength oscillated by a wavelength-sweeping light source. Japanese Patent Application Laid-Open No. 2013-156229 discusses obtaining of a tomographic image from which such a noise component is removed by signal processing.

SUMMARY OF THE INVENTION

According to an aspect of the present invention, an ophthalmic imaging apparatus that captures a tomographic image of an subject's eye based on light obtained by combining a return light with a reference light, the return light being from the subject's eye when irradiated with a measurement light, the reference light corresponding to the measurement light includes a first optical fiber disposed in an optical path of the reference light and including a light guide portion for guiding the reference light, and a second optical fiber disposed in an optical path of the measurement light and including a light guide portion for guiding the measurement light, wherein a diameter of each of the light guide portions of ejection ends of the first optical fiber and the second optical fiber is larger than a diameter of a light guide portion in a position different from a position of each of the ejection ends.

Further features of the present invention will become apparent from the following description of example embodiments with reference to the attached drawings.

DESCRIPTION OF THE EMBODIMENTS

When a desirable tomographic image is to be obtained at high speed, a load of signal processing is desirably low. For example, the signal processing may be performed to reduce noise. In such a case, display of a tomographic image can be delayed. Moreover, in a case where noise appears over an observation object such as a retina, reduction of such noise by the signal processing is difficult.

Meanwhile, a scattering of light by an optical member of an ophthalmic imaging apparatus is known as a cause of noise. In general, the ophthalmic imaging apparatus includes an optical fiber. There is a possibility that noise may be generated by interference of light scattered by an ejection end of the optical fiber with reference light.

Accordingly, one of advantages of example embodiments is that an ejection end of an optical fiber is configured in such a manner that noise in a tomographic image caused by light scattered by the ejection end of the optical fiber is reduced.

Hereinafter, the example embodiments are described with reference to drawings. However, the example embodiments are not limited thereto. As long as the ejection end of the optical fiber is configured in such a manner that noise in a tomographic image caused by light scattered by the ejection end of the optical fiber can be reduced, any configuration can be employed.

Hereinafter, a first example embodiment is described. In the present example embodiment, an example in which a tomographic image is generated from optical interference signals is illustrated.

[Overall Configuration of Ophthalmic Imaging Apparatus]

Figure 1:
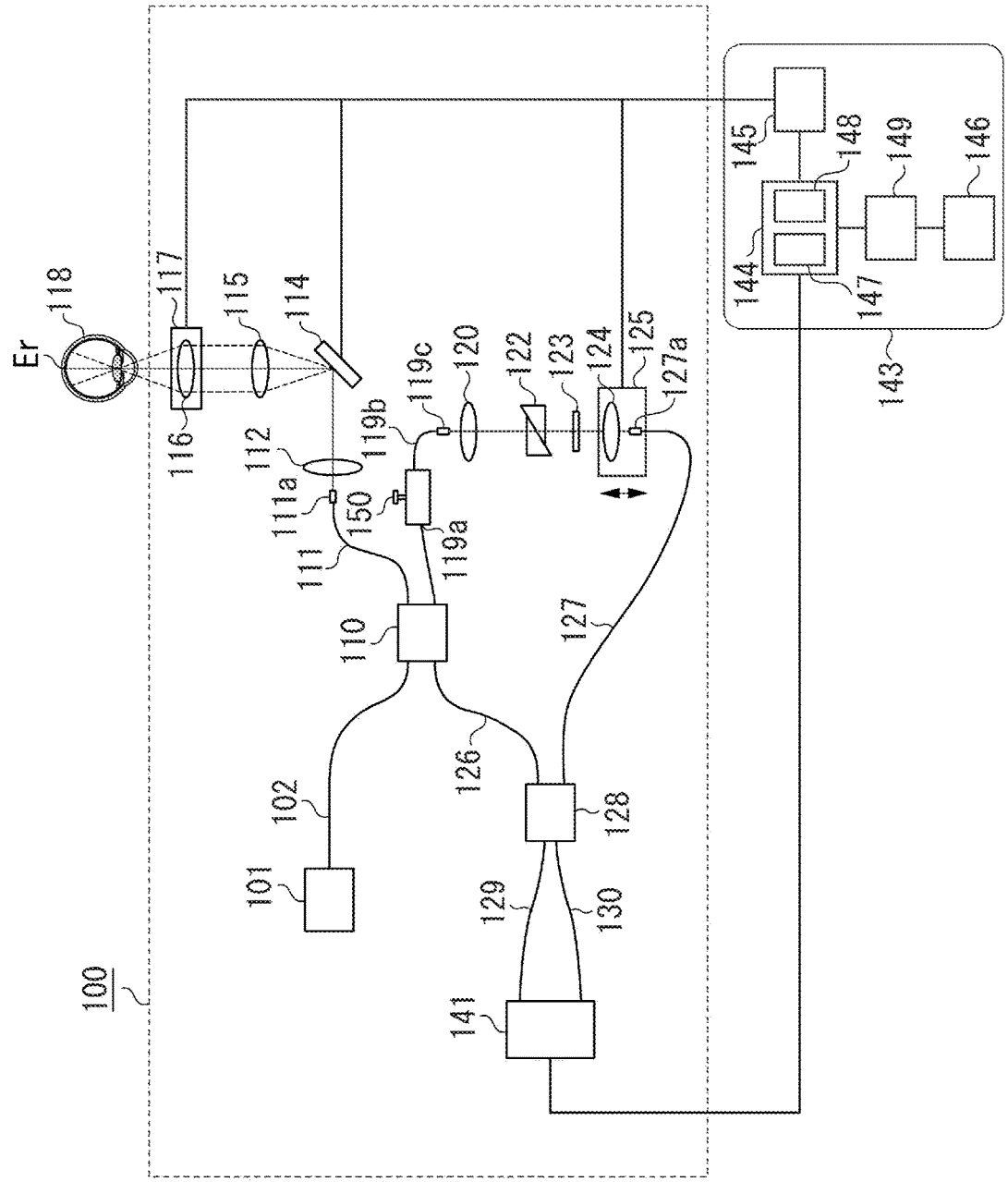
FIG. 1 is a schematic diagram illustrating an overall configuration of an ophthalmic imaging apparatus according to a first example embodiment.

FIG. 1 is a diagram illustrating an example of a configuration of an ophthalmic imaging apparatus that captures a tomographic image of a subject's eye by using OCT according to the present example embodiment. The ophthalmic imaging apparatus includes a control unit 143 and an OCT apparatus (optical coherence tomographic image obtaining unit) 100 that obtains an optical coherence tomographic signal. The control unit 143 includes a signal processing unit 144, a signal acquisition control unit 145, a display control unit 149, and a display unit 146. Moreover, the signal processing unit 144 includes an image generating unit 147 and a map generating unit 148.

<Configuration of OCT Apparatus 100>

A configuration of the OCT apparatus 100 is described. A light source 101 is a wavelength-sweeping light source. For example, the light source 101 emits light while sweeping the light with a sweeping center wavelength of 1050 nm and a sweeping width of 100 nm. The light source 101 includes a cavity (not illustrated). The cavity is disposed inside the light source 101 or outside the light source 101. The cavity has a cavity length of 50 mm, for example. The ophthalmic imaging apparatus according to the present example embodiment is a swept source optical coherence tomography (SS-OCT) apparatus with a wavelength-sweeping light source capable of changing an oscillation wavelength. However, another type of an OCT apparatus (e.g., a spectral domain OCT (SD-OCT) apparatus) can be used.

The light ejected from the light source 101 is guided to a beam splitter 110 via an optical fiber 102, and then branched into measurement light (also referred to as OCT measurement light) and reference light (also referred to as reference light corresponding to the OCT measurement light). The beam splitter 110 has a branch ratio of 70:30 (the branch ratio of reference light to measurement light is 70:30). The branched measurement light is ejected via an optical fiber 111 that is one example of a second optical fiber disposed in an optical path of the measurement light, and is then formed into parallel light by a collimator 112. The optical fiber 111 has an end portion 111a that will be described below. The measurement light formed into the parallel light enters a subject's eye 118 via a galvano scanner 114, a scan lens 115, and a focus lens 116. The galvano scanner 114 scans the measurement light on a funds Er of the subject's eye 118. Although the galvano scanner 114 is described as having a single mirror for the sake of simplicity, the actual galvano scanner 114 includes two galvano scanners: an X-axis scanner and a Y-axis scanner (not illustrated), so that the fundus Er of the subject's eye 118 is scanned in a raster manner. Moreover, the focus lens 116 is fixed on a stage 117, and movement of the focus lens 116 on the stage 117 in an optical axis direction enables a focus adjustment. The galvano scanner 114 and the stage 117 are controlled by the signal acquisition control unit 145. Such control enables the measurement light to be scanned on the fundus Er of the subject's eye 118 in a desired range (also referred to as a tomographic image obtaining range, a tomographic image obtaining position, or a measurement light irradiation position).

The OCT apparatus 100 desirably has a tracking function of detecting a movement of the fundus Er and causing a mirror of the galvano scanner 114 to track the movement of the Er to perform scanning although the tracking function is not described in detail in the present example embodiment. Such tracking can be performed by using a general technique. The tracking can be performed in a real time manner or a post-processing manner. If the real-time tracking is performed, there is a method using a scanning laser ophthalmoscope (SLO), for example. According to the method, two-dimensional images (fundus surface images) on a plane perpendicular to an optical axis are obtained over time using the SLO to extract a feature area such as vascular bifurcation from the images. A movement of the feature area in the obtained two-dimensional images is calculated as a moving amount of the fundus Er, and the calculated moving amount is fed back to the galvano scanner 114. Thus, the real-time tracking can be performed.

The measurement light, when entering the subject's eye 118, is focused on the fundus Er by the focus lens 116 arranged on the stage 117. The measurement light emitted onto the fundus Er is reflected/scattered by each of retina layers, and then returns to the beam splitter 110 via the aforementioned optical path. The return light of the measurement light, which has entered the beam splitter 110, passes through an optical fiber 126 and enters a beam splitter 128. On the other hand, the reference light branched by the beam splitter 110 passes through an optical fiber 119a, a polarization controller 150, and an optical fiber 119b and is ejected at an optical fiber end portion 119c, and the ejected light is formed into parallel light by a collimator 120. The optical fiber end portion 119c is described in detail below. The polarization controller 150 can change polarization of the reference light to a desired polarization state. The reference light passes through a dispersion-compensating glass 122, a neutral-density (ND) filter 123, and a collimator 124 and enters an optical fiber end portion 127a of an optical fiber 127. The collimator 124 and one end of the optical fiber 127 are fixed on a coherence gate stage 125, and are controlled by the signal acquisition control unit 145 so as to be driven in an optical axis direction according to an eye axis length of a subject. Herein, each of these optical fibers arranged in the optical path of the reference light is one example of a first optical fiber. In the present example embodiment, a mechanism for changing an optical path length of the reference light is provided. However, a different mechanism may be provided as long as a difference in optical path lengths of the reference light and the measurement light can be changed. Moreover, the present example embodiment has been described using an example in which the optical fiber end portion 119c of a light projecting side and the optical fiber end portion 127a of a light receiving side are disposed opposite to each other in a straight line. However, the optical path may be folded by a reflection mirror.

After passing the optical fiber 127, the reference light enters the beam splitter 128. In the beam splitter 128, return light of the measurement light and the reference light are combined to generate interference light, and then the interference light is split into two. The two split rays of the interference light have phases that are reversed from each other (hereinafter referred to as a positive component and a negative component). The positive component of the split interference light passes through an optical fiber 129 and enters one input port of a detector 141. On the other hand, the negative component of the interference light passes through an optical fiber 130 and enters the other input port of the detector 141. The detector 141 serves as a differential detector. When two interfering signals of which phases that are inverted by 180 degrees are input, the detector 141 removes a direct current component to output only an interfering component. The interfering signal detected by the detector 141 is output as an electrical signal according to light intensity, and the electrical signal is input to the signal processing unit 144 serving as one example of a tomographic image generating unit.

An analog-to-digital (A/D) converter for converting a detected interfering signal from an analog signal to a digital signal is preferably disposed at a following stage of the detector 141. Moreover, a clock generating unit for generating a clock signal used for sampling of the interfering signal by the A/D converter preferably includes an interferometer including a first optical path and a second optical path having an optical path length difference with respect to the first optical path. Herein, the optical path length difference corresponds to a frequency of the clock signal. Herein, light ejected from the light source 101 and then split at a preceding stage of the beam splitter 110 is preferably guided to the interferometer of the clock generating unit. However, another configuration may be employed as long as one portion of the light ejected from the light source 101 is guided to the interferometer of the clock generating unit.

Accordingly, even if wavelength-sweeping stability of the light source is low, the sampling can be performed at a substantial wavenumber interval. Moreover, a trigger generating unit (e.g., a fiber bragg grating (FBG) and an etalon) is preferably disposed. The trigger generating unit generates a trigger signal using one portion of the light ejected from the light source 101. The trigger signal is generated for recognition of the start and end of every A-scan for a tomographic image of a subject's eye.

Moreover, in the present example embodiment, as long as the light source 101 can change a wavelength of light, the light source 101 is not limited thereto. A wavelength of light from the light source 101 needs to be continuously changed so that information of an object is obtained using the OCT apparatus. In the present example embodiment, a light source such as an external-cavity-type wavelength-sweeping light source using a diffraction grating or a prism, and various external-cavity-type light sources using a cavity-length-variable Fabry-Perot tunable filter can be used as the light source 101. Alternatively, a superstructure-grating distributed Bragg reflector (SSG-DBR) that changes a wavelength by using sampled grading, or a wavelength-variable vertical cavity surface emitting laser (VCSEL) using a micro-electro-mechanical system (MEMS) mechanism (MEMS-VCSEL) can be used. Moreover, a fiber laser can be used. Examples of the fiber laser include a fiber laser employing a dispersion tuning method, and a fiber laser employing a fourier domain mode locking method. An example of the external-cavity-type wavelength-sweeping light source using a diffraction grating or a prism includes a wavelength-sweeping light source that disperses light by using a diffraction grating disposed in a cavity and continuously changes a wavelength of light to be ejected by using a polygon mirror or a member including a stripe-shaped reflection mirror disposed on a rotary disk. Moreover, the VCSEL serving as a surface emitting laser generally includes a lower reflector, an active layer, and an upper reflector that are arranged in this order. The VCSEL also includes a gap between the active layer and the upper reflector. The VCSEL changes an axial position of at least one of the upper reflector and the lower reflector to change a wavelength of light to be ejected.

<Control Unit 143>

The control unit 143 for comprehensively controlling the ophthalmic imaging apparatus is described. The control unit 143 includes the signal processing unit 144, the signal acquisition control unit 145, the display unit 146, and the display control unit 149. The signal processing unit 144 includes the image generating unit 147 and the map generating unit 148. The image generating unit 147 has a function of generating a luminance image from an electrical signal to be transmitted, whereas the map generating unit 148 has a function of generating layer information (segmentation of a retina) from the luminance image. The signal acquisition control unit 145 controls each of the units as described above. The signal processing unit 144, based on a signal output from the detector 141, generates an image, analyzes the generated image, and generates visual information of an analysis result. Moreover, the image or the analysis result generated by the signal processing unit 144 is transmitted to the display control unit 149, so that the display control unit 149 displays the image or the analysis result on the display unit 146. Herein, the display unit 146 is, for example, a display such as a liquid crystal display. Image data generated by the signal processing unit 144 is transmitted to the display control unit 149. After being transmitted to the display control unit 149, the image data can be transmitted to the display unit 146 in a wired or wireless manner. In the present example embodiment, the control unit 143 includes the display unit 146. However, the present example embodiment is not limited thereto. The display unit 146 may be disposed separately from the control unit 143. For example, the display unit 146 may be a tablet as one example of a device that can be carried by a user. In such a case, the tablet as the display unit 146 preferably has a touch panel function, so that operations such as movement of an image display position, enlargement and reduction of an image, and a change of a displayed image can be performed on the touch panel.

Accordingly, information about a tomography in a certain point of the subject 118 is obtained. Such acquisition of information about the tomography in a depth direction of the subject 118 is called A-scan. Moreover, information about the tomography of the subject in a direction perpendicular to the A-scan, that is, a scanning direction for acquisition of a two-dimensional image is called B-scan. Moreover, scanning performed in a direction perpendicular to any of the scanning directions for the A-scan and the B-scan is called C-scan. When a three-dimensional tomographic image is obtained, two-dimensional raster scanning may be performed on a fundus surface. In such a case, a high-speed scanning direction is called B-scan, and a low-speed scanning direction in which scanning is performed by arranging the B-scan in a perpendicular direction thereof is called C-scan. The performance of the A-scan and the B-scan can obtain a two-dimensional tomographic image, whereas the performance of the A-scan, the B-scan, and the C-scan can obtain a three-dimensional tomographic image. Each of the B-scan and the C-scan is performed by the aforementioned galvano scanner 114.

Each of the X-axis scanner (not illustrated) and the Y-axis scanner (not illustrated) includes a deflecting mirror that is disposed such that rotation axes thereof are perpendicular to each other. The X-axis scanner performs scanning in an X-axis direction, whereas the Y-axis scanner performs scanning in a Y-axis direction. Each of the X-axis direction and the Y-axis direction is perpendicular to an eye axis direction of an eyeball, and the X-axis direction and the Y-axis direction are perpendicular to each other. Moreover, a line scanning direction such as the B-scan and the C-scan, and the X-axis direction or the Y-axis direction may not necessarily be matched. Accordingly, a line scanning direction of the B-scan or the C-scan can be determined as necessary according to a two-dimensional tomographic image or a three-dimensional tomographic image intended to be captured.

Next, a description is given of an ejection end of an optical fiber and an effect thereof according to the present example embodiment. First, a coherence revival ghost is described to describe the effect of the ejection end of the optical fiber. The term "coherence revival" represents that a coherence gate can behave as if a plurality of coherence gates is present in a cavity length period of a wavelength-sweeping light source. The term "coherence revival ghost" represents an image that appears as a ghost in a tomographic image due to interference of a revived coherence gate with reflected light from each optical member disposed in the ophthalmic imaging apparatus. The coherence revival ghost markedly appears if a wavelength-sweeping light source is the external-cavity-type wavelength-sweeping light source described above. The external-cavity-type wavelength-sweeping light source constantly has a multiplex mode corresponding to a cavity length, and sequentially selects a wavelength of light to be ejected therefrom. Thus, the coherence revival corresponding to a cavity length occurs. On the other hand, for example, the MEMS-VCSEL drives a mirror by using a MEMS to sequentially generate light to be ejected.

Particular examples are described as follows. The external-cavity-type wavelength-sweeping light source causes light to resonate with a cavity including a member such as a mirror and a filter inside or outside the light source. In a case where the light ejected from the wavelength-sweeping light source is branched and then combined, a difference in optical path lengths of the two rays of light may become an integral multiple of a cavity length. In such a case, interference occurs. Such interference is called coherence revival. In the OCT, an image is obtained using interference that occurs when an optical path length of the measurement light and an optical path length of the reference light are equal to each other. In the SS-OCT using the wavelength-sweeping light source with a cavity, interference occurs due to coherence revival even if a difference in optical path lengths of rays of light to be combined is an integral multiple of a cavity length. The interference may occur due to other than the combination of the predetermined measurement light and reference light. In such a case, the interference becomes noise. Such noise is called a coherence revival ghost. An example of the light other than the measurement light and the reference light includes reflected light from an interface between an optical element and air in an optical path.

Moreover, since higher sensitivity, larger imaging range, and higher speed of the SS-OCT are demanded, the coherence revival ghost needs to be further dealt with. That is, as for the higher sensitivity, if an ophthalmic imaging apparatus has a sensitivity that exceeds 90 dB in a signal-to-noise ratio, a ghost having an intensity (−80 dB) between an intensity similar to a reflectance (approximately $10^{-6}$ (approximately −60 dB)) in a fundus and an intensity lower than the reflectance by two digits becomes noticeable. Meanwhile, enlargement of the imaging range may cause the imaging range to be broader than a cavity length of a light source. In such a case, adjustment of an optical path length cannot provide a ghost in an area outside the imaging range. Consequently, the imaging range can be limited to eliminate the ghost.

Figure 6A:
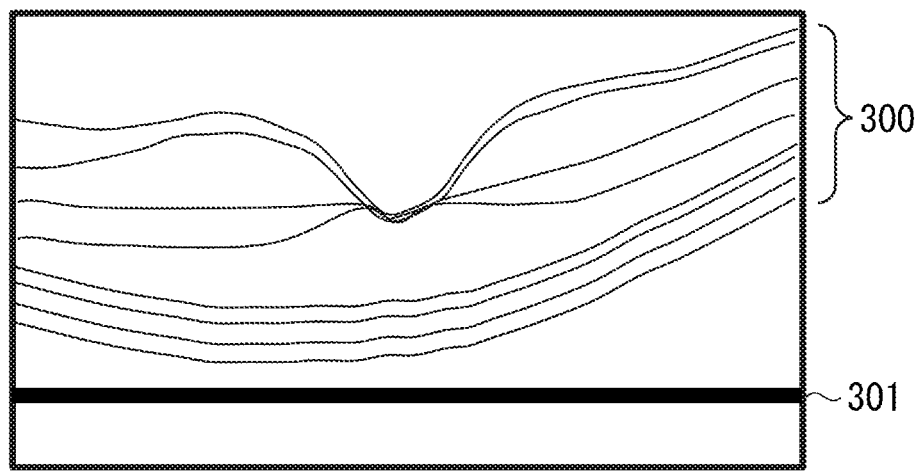
FIGS. 6A and 6B are diagrams each illustrating one example of an optical coherence tomographic image obtained using optical coherence tomography (OCT).
Figure 6B:
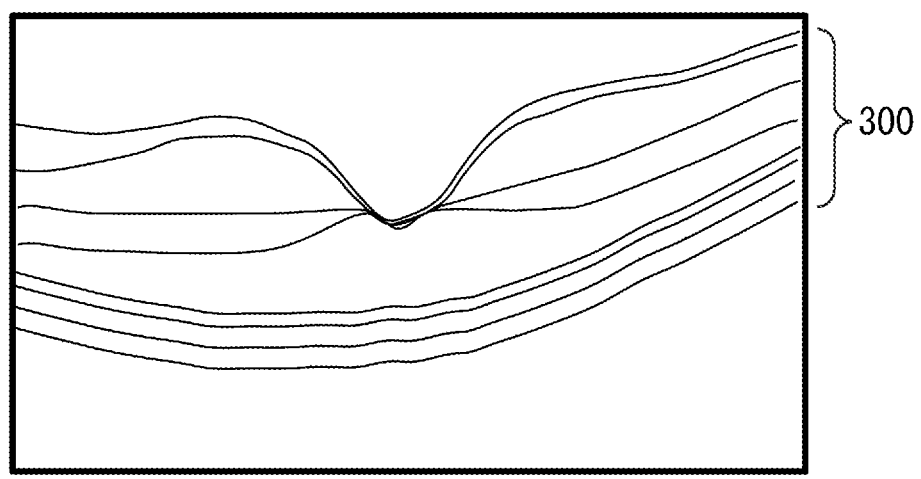
Figure 8:
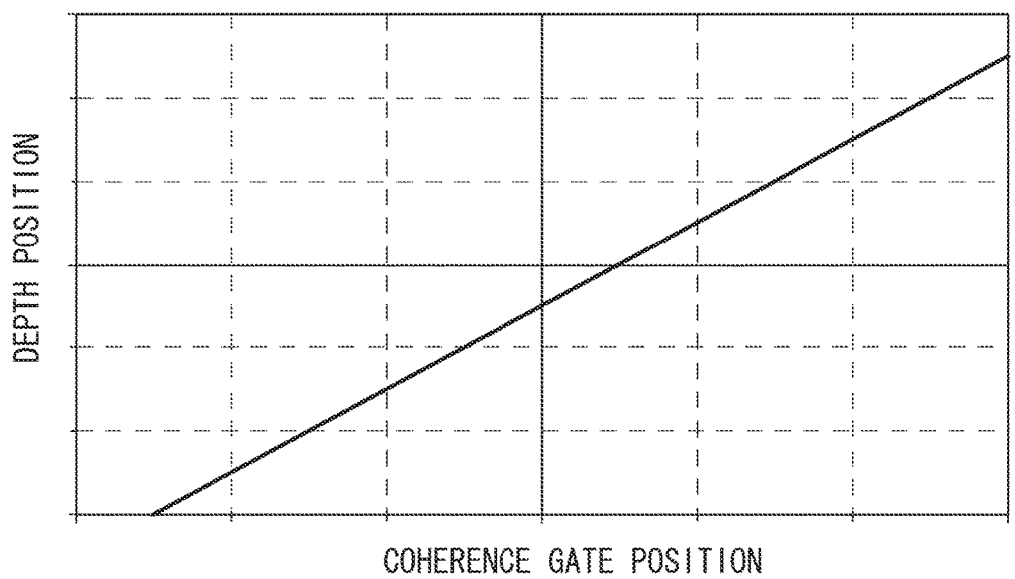
FIG. 8 is a diagram illustrating a relationship between a coherence gate stage position and a coherence revival ghost position.

Herein, FIG. 6A illustrates an example in which a coherence revival ghost is present in a tomographic image, whereas FIG. 6B illustrates an example in which a coherence revival ghost is not preset in a tomographic image. In the tomographic image as illustrated in FIG. 6A, a coherence revival ghost 301 overlaps reflected signals 300 in a belt-like manner. The reflected signals 300 are signals reflected from a retina. FIG. 8 illustrates a relationship between a position of the coherence gate stage 125 and a position of the coherence revival ghost where the coherence revival ghost is present in the example. In FIG. 8, a horizontal axis indicates a position of the coherence gate stage 125. Assume that the center in the horizontal axis is a reference position, and a rightward direction corresponds to a direction in which an optical path length of reference light is increased. A vertical axis illustrated in FIG. 8 corresponds to a depth direction (a vertical direction) of the tomographic image illustrated in FIG. 6A. A solid line represents a depth position of the coherence revival ghost 301 with respect to a position of the coherence gate stage 125. As illustrated in FIG. 8, a position of the coherence revival ghost 301 is changed with movement of the coherence gate stage 125. Similarly, the reflected signal 300 from the retina moves. Thus, such a movement may interrupt observation depending on a position of the ghost. Herein, the position of the coherence revival ghost depends on a difference in optical path lengths of rays of light interfering with each other. The coherence revival ghost appears in a position in which an optical path length difference is an integral multiple of a cavity length of the light source. The imaging range in the depth direction of the OCT apparatus is the sum of a range in a depth direction of a tomographic image and an adjustment range of the reference light path. If the imaging range of the OCT apparatus is broader than a cavity length of the light source, a difference in the optical path lengths becomes an integral multiple of the cavity length of the light source in any position of the imaging range. Consequently, a ghost occurs within the imaging range.

Figure 2:
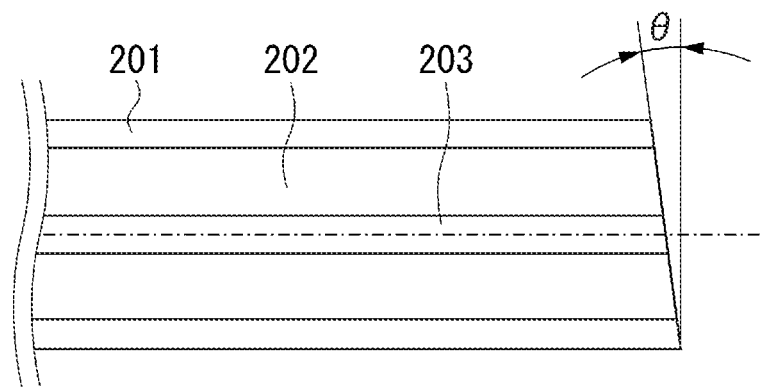
FIG. 2 is a schematic diagram illustrating a configuration of an end surface of an optical fiber.

The inventors have found that the coherence revival occurs when an optical fiber end portion for projecting and receiving measurement light and an optical fiber end portion for projecting reference light interfere with the reference light. A description is given of a reason that the optical fiber end portion serves as a reflection portion. An optical fiber that ejects light to the air has an end surface that is obliquely ground to reduce reflection. FIG. 2 illustrates an example of the oblique grinding. In general, a grinding angle θ is approximately 8 degrees. A clad 202 and a core 203 through which light passes are arranged inside a ferrule 201 that retains the optical fiber. Since the clad 202 and the core 203 have different refractive indexes, the light is totally reflected at a boundary between the core 203 and the clad 202. The light guided through the core 203 is ejected from the end portion of the optical fiber. A reflection loss in the optical fiber end portion obliquely ground is between −50 dB and −60 dB. Moreover, in a case where an anti-reflection film is arranged in the optical fiber end portion, a reflection is reduced by approximately one digit in terms of the value of the amount.

An interference system of the present example embodiment includes the optical fiber end portion 111a for projecting and receiving measurement light, and the optical fiber end portion 119c for projecting measurement light. If light is reflected by the optical fiber end portion 111a for projecting and receiving the measurement light, the reflected light passes through the optical fiber 111, the beam splitter 110 and the optical fiber 126, and is then combined with the reference light in the beam splitter 128. Similarly, if light is reflected by the optical fiber end portion 119c for projecting the reference light, the reflected light passes through the optical fiber 119, the beam splitter 110 and the optical fiber 126, and is then combined with the reference light in the beam splitter 128. Since a reflection loss in the optical fiber end portion is between −50 dB and −60 dB with respect to the reflectance (approximately $10^{-6}$ (approximately −60 dB)) in the fundus, such intensity cannot be ignored. When a difference in optical path lengths of the reflected light and the reference light in the optical fiber end portions becomes an integral multiple of the cavity length of the light source due to movement of the coherence gate stage 125, interference occurs. Accordingly, a coherence revival ghost occurs in a tomographic image. In FIG. 6A, the coherence revival ghost appears only in one position. However, the coherence revival ghost can appear in a plurality of positions depending on an imaging range and a relationship between a cavity length of the light source and an optical path length difference. For example, in a case where there is a plurality of positions in which a difference in optical path lengths of the reflected light and the reference light in the optical fiber ends is an integral multiple of a cavity length of the light source within an imaging range, a ghost occurs in each of such positions. Moreover, in a case where there is a plurality of reflection portions, a plurality of coherence revival ghosts can occur. Herein, the reflected light in the optical fiber end portion needs to have a quantity that is sufficiently small with respect to the measurement light from the fundus so that the coherence revival ghost is reduced. A rough standard of the sufficiently small light quantity can be a quantity of light at a detection limit (noise floor) of a detector of the OCT apparatus. Since the ophthalmic imaging apparatus needs to have a sensitivity of approximately 90 dB in the signal-to-noise ratio to obtain a tomographic image of a fundus, a reflection loss in the optical fiber end portion can be −90 dB or less.

Figure 3A:
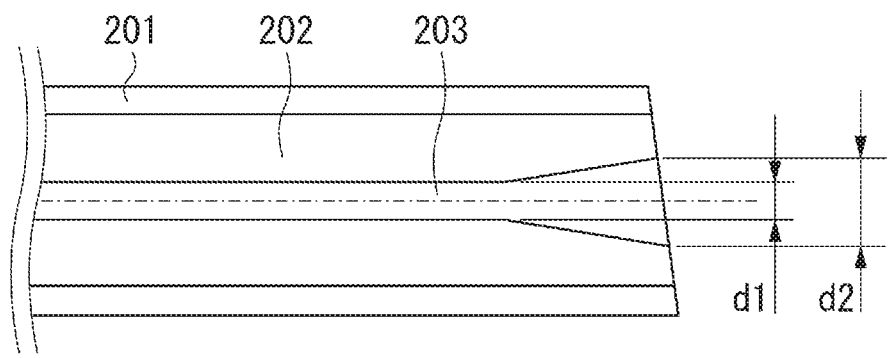
FIGS. 3A and 3B are schematic diagrams each illustrating the end surface of the optical fiber according to the first example embodiment.
Figure 3B:
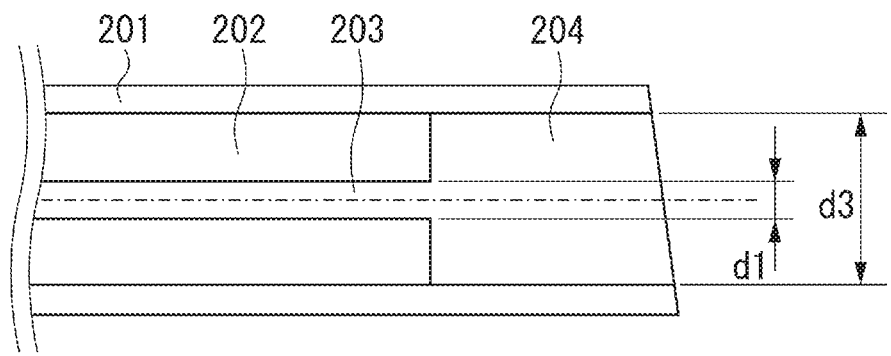

Herein, an optical fiber ejection portion according to the present example embodiment is described. In the present example embodiment, a light guide portion in at least one of optical fiber ejection ends of the optical fiber end portion 111a for projecting and receiving measurement light and an optical fiber end portion 127c for projecting reference light has a diameter larger than a diameter (a core diameter) of a light guide portion of the optical fiber. Such a larger diameter of the ejection end reduces reflection. Next, a description is given of a case in which a diameter of the light guide portion in the ejection end of the optical fiber is larger than a core diameter of the optical fiber according to the present example embodiment. Such a case is described with reference to FIGS. 3A and 3B that each illustrate the end portion of the optical fiber. The clad 202 and the core 203 as one example of a light guide portion for guiding light are arranged inside the ferrule 201 which retains the optical fiber. In the present example embodiment, a diameter in the ejection end of the optical fiber is larger than that of the core 203. FIG. 3A illustrates an example of a thermally-diffused expanded core (TEC) processed optical fiber, and FIG. 3B illustrates an example in which a coreless optical fiber 204 is spliced to the ejection end. Although a TEC process and splice of the coreless optical fiber are not well known as optical fiber end processing in the field of OCT or ophthalmology, the TEC process and the coreless optical fiber splice are known in the other fields. The TEC process locally increases a mode field diameter of an optical fiber by two to three times and reduces a numerical aperture (NA) by using TEC technique. Since the TEC-processed optical fiber is arranged in a facing manner, an allowable range with respect to imperfect alignment or a gap is increased, and a splice loss is reduced (e.g., Japanese Patent Application Laid-Open No. 2008-191369). Moreover, in the coreless optical fiber splice, fusion splice of the coreless optical fiber to a leading end of the optical fiber is performed. The arrangement of the coreless optical fiber can reduce reflection in an end surface (e.g., Japanese Patent Application Laid-Open No. 7-281054).

The TEC-processed optical fiber has a core diameter d2 in an ejection end, and the core diameter d2 is increased by two to three times by thermal diffusion with respect to a core diameter d1 in the optical fiber. Although the core diameter d1 can vary depending on a wavelength to be used, for example, the core diameter d1 is approximately 6 μm if a wavelength has a 1-μm band. The TEC process enables the core diameter d2 in the ejection end to be increased to approximately 12 μm to 18 μm. The use of the predetermined TEC process increases a mode field diameter of the optical fiber, and reduces a NA. As illustrated in FIG. 3A, the light guide portion of the optical fiber is configured such that a diameter thereof is gradually increased as the light guide portion approaches the ejection end of the optical fiber.

Moreover, the coreless optical fiber 204 having a refractive index that is substantially similar to that of the core 203 is spliced to a leading end of the core 203. In FIG. 3B, the core 203 is one example of a first area having a first diameter in a position different from a position of the ejection end of the optical fiber, and the coreless optical fiber 204 is one example of a second area having a second diameter that is larger than the first diameter in the ejection end. The clad 202 and the core 203 can be spliced to the coreless optical fiber 204 by fusion. If a diameter d3 of the coreless optical fiber 204 is substantially the same as that of the clad 202, the coreless optical fiber 204 can be arranged inside the ferrule 201. Typically, the diameter d3 of the coreless optical fiber 204 or the diameter of the clad 202 is 125 μm.

Figure 4:
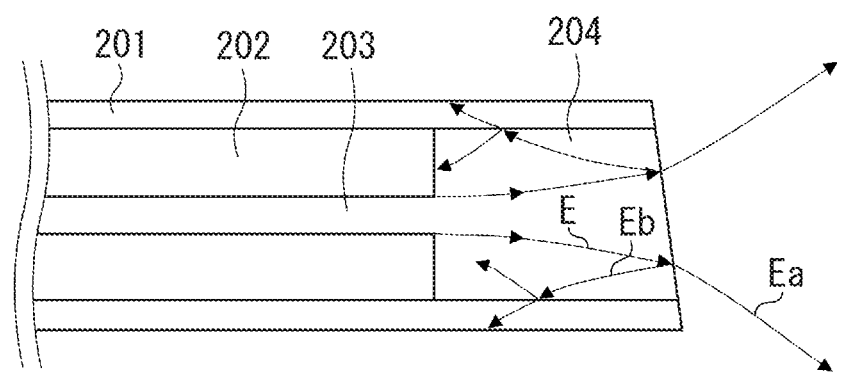
FIG. 4 is a schematic diagram illustrating spread of light in the optical fiber according to the first example embodiment.

FIG. 4 illustrates how light spreads when the coreless optical fiber 204 is spliced. In FIG. 4, light E ejected from the core 203 is separated into emittance light Ea and reflected light Eb on an end surface of the coreless optical fiber 204. The reflected light Eb spreads inside the coreless optical fiber 204. When the reflected light Eb spreads and reaches an interface between the coreless optical fiber 204 and the ferrule 201, one portion thereof is transmitted through the ferrule 201, and one portion thereof is reflected. Since the reflected light Eb is suppressed to directly enter the core 203, light returning to the core 203 is more reduced compared to the case in which the normal oblique grinding is used. A length of the coreless optical fiber 204 can be set such that the light E ejected from the core 203 does not reach the ferrule 201 in the coreless optical fiber 204. How the beam spreads in the coreless optical fiber 204 can be calculated using a NA and a mode field diameter d1 of the core 203, and a refractive index n of the coreless optical fiber 204. A length of the coreless optical fiber 204 can be determined based on the spread of the beam in the coreless optical fiber 204.

Figure 5:
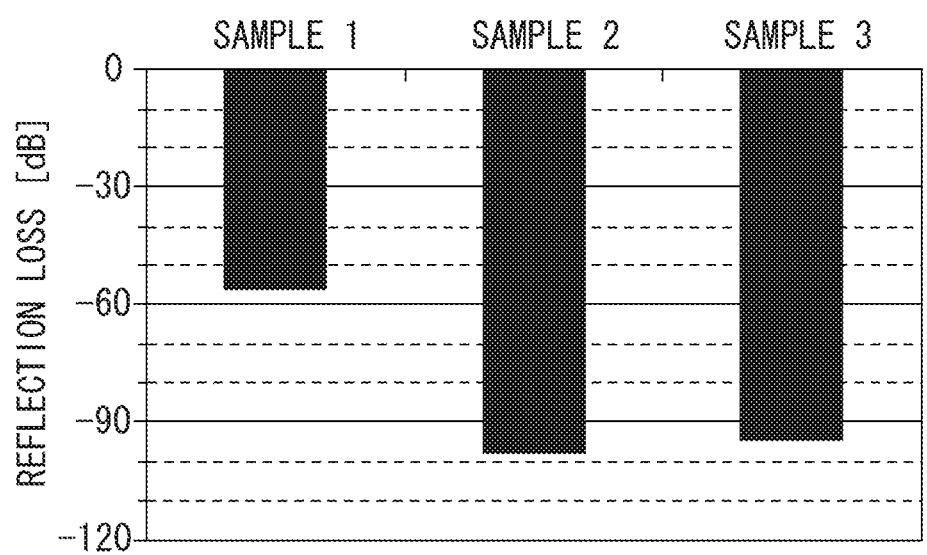
FIG. 5 is a diagram illustrating a reflection loss in the end surface of the optical fiber.

A reflection quantity in a reflection suppressing process is described with reference to FIG. 5 that illustrates a reflection loss in an ejection end of an optical fiber. In FIG. 5, a sample 1 indicates a representative value of reflection loss in an ejection end having an angle of 8 degrees by surface grinding. The sample 1 has a reflection loss of approximately between −50 dB and −60 dB including variations. A sample 2 indicates a representative value of reflection loss in an ejection end of a TEC-processed optical fiber, and has a reflection loss of approximately between −90 dB to −100 dB. A sample 3 indicates a representative value of reflection loss in an ejection end of a coreless optical fiber, and has a reflection loss of approximately between −90 dB to −100 dB. Each of the TEC-processed optical fiber and the coreless optical fiber has the ejection end having an 8-degree angle by surface grinding.

The inventors have found that the TEC-processed optical fiber has an effect in reducing reflection. The TEC process can reduce reflection by the following reasons. Since an end portion of the core 203 is tapered by the TEC process, it is conceivable that a quantity of light reflected on the optical fiber end surface and returning to the core 203 is reduced. In the present example embodiment, a light guide portion in at least one of ejection ends of the optical fiber end portion 111a for projecting and receiving measurement light and the optical fiber end portion 127c for projecting reference light has a diameter larger than a core diameter of the optical fiber. Such an arrangement can reduce a coherence revival ghost due to reflection by the optical fiber end portion. Such reduction can be applied if the coherence revival ghost due to reflection in one of the optical fiber end portions is provided in an imaging range. FIG. 6B illustrates a tomographic image according to the present example embodiment. The tomographic image without a coherence revival ghost is obtained as illustrated in FIG. 6B, unlike the example in which the coherence revival ghost is present in the tomographic image illustrated in FIG. 6A. Moreover, a coherence revival ghost caused by reflection in the other optical fiber in which reflection is not reduced may occur in the imaging range. Even in such a case, reduction of the ghost on one side can reduce a calculation load for which the ghost is reduced by signal processing.

The optical fiber end portion for reducing reflection can be disposed in each of both ends instead of one of the ends. A diameter of a light guide portion in an optical fiber ejection end of each of the optical fiber end portion 111a for projecting and receiving measurement light and the optical fiber end portion 127c for projecting reference light is larger than an optical fiber core diameter. Such an arrangement can reduce coherence revival ghosts caused by reflection in the optical fiber end portion 111a and the optical fiber end portion 127a.

Herein, each of the above-described configurations in which a diameter of the light guide portion in the optical fiber ejection end is larger than the optical fiber core diameter can be applied by itself, or they can be applied in combination as necessary. A coreless optical fiber is preferably spliced to the optical fiber end portion 111a for projecting and receiving measurement light, and a TEC-processed optical fiber is preferably arranged in the optical fiber end portion 119c for projecting reference light by the following reasons. The reasons for arrangement of the TEC-processed optical fiber in the optical fiber end portion include enhancement of coupling efficiency of optical fibers. That is, light that intends to enter the optical fiber ejection end can be readily taken in. Moreover, a TEC-processed optical fiber can be arranged in the optical fiber end portion 127a for receiving reference light. The arrangement of the TEC-processed optical fiber in a counter optical fiber end portion can enlarge an allowable range with respect to imperfect alignment or a gap, so that coupling efficiency of the optical fibers can be enhanced. Therefore, the TEC-processed optical fiber is preferably arranged in the optical fiber end portion for projecting and receiving reference light. Moreover, the coreless optical fiber is preferably spliced to the optical fiber end portion 111a for projecting and receiving measurement light. When the coreless optical fiber is spliced, a variation in the NA or the mode field diameter of the ejection portion is smaller than that when a TEC-processed optical fiber is spliced. However, if the TEC-processed optical fiber is used in the optical fiber ejection portion for the measurement light, a variation in spot size on a fundus is likely to occur. That is, the variation in the NA or the mode field diameter causes a variation in spot diameter of the beam condensed on the fundus Er. Since the variation in the spot diameter causes a variation in transverse resolution, the variation is preferably smaller. Since the TEC-processed optical fiber has a mode field diameter increased by thermal diffusion processing, a variation in processing causes a relative variation in the mode field diameter or the NA to tend to occur. Hence, the coreless optical fiber is preferably spliced to the optical fiber end portion 111a for projecting and receiving measurement light.

Alternatively, the TEC-processed optical fiber and a zoom lens may be combined. Arrangement of the zoom lens for changing a diameter of the beam ejected from the optical fiber end portion 111a can correct a variation in the diameter.

In the present example embodiment, an image capturable range of the ophthalmic imaging apparatus in a depth direction of a subject's eye is preferably longer than a cavity length of a wavelength-sweeping light source. That is, even if a coherence revival ghost occurs in a tomographic image, such a ghost can be reduced. The ophthalmic imaging apparatus does not need to be optically designed to reduce a ghost, and thus the image capturable range in the depth direction can be enlarged.

Figure 7:
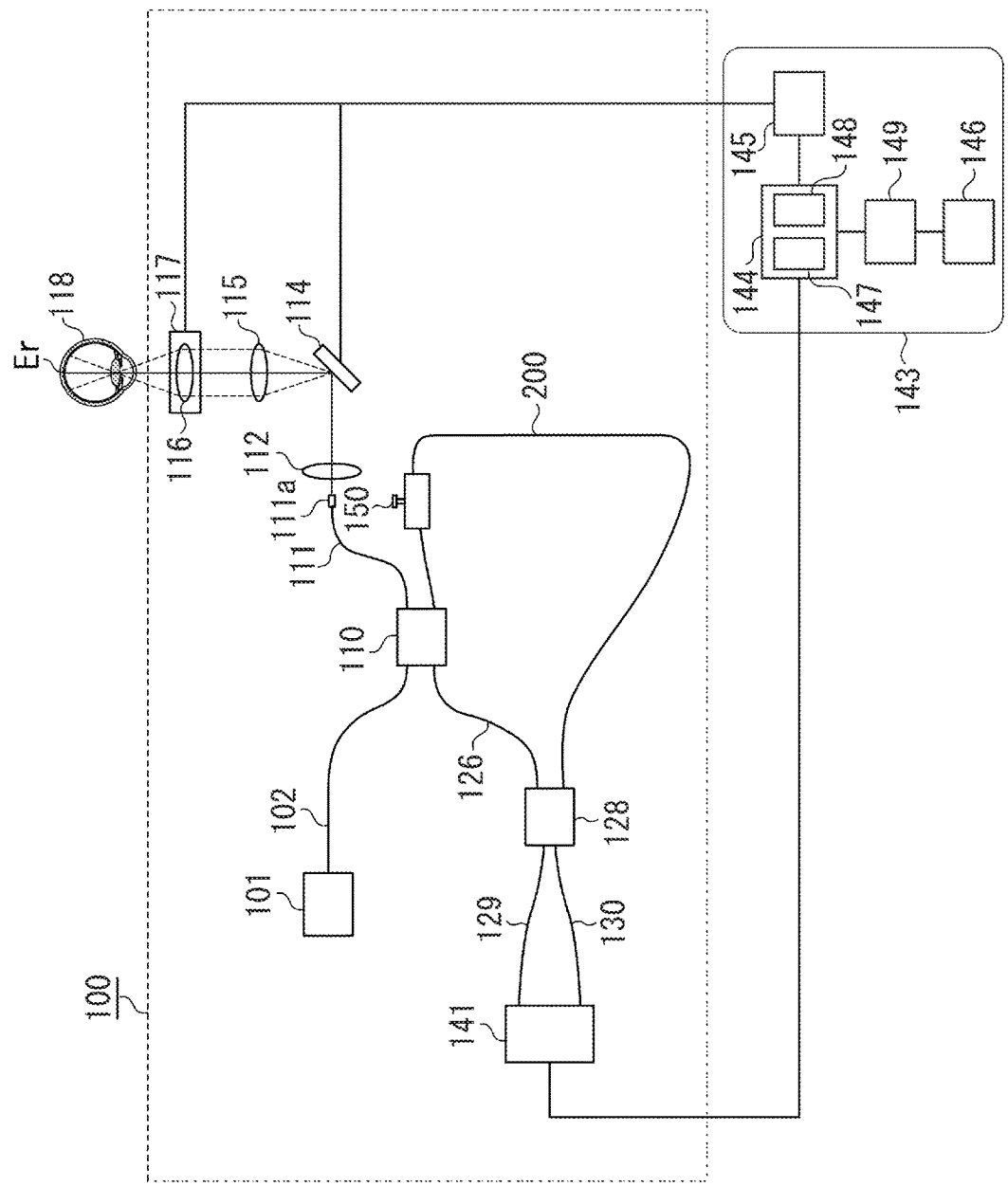
FIG. 7 is a schematic diagram illustrating an overall configuration of an ophthalmic imaging apparatus according to a second example embodiment.

A second example embodiment is described with reference to FIG. 7. Hereinafter, components and configurations that differ from those of the first example embodiment are described.

Reference light branched by a beam splitter 110 passes through an optical fiber 200 and enters a beam splitter 128. The optical fiber 200 is one example of a first optical fiber disposed in an optical path of the reference light. In the beam splitter 128, return light of measurement light and the reference light are combined and formed into interference light, and then the interference light is split into two. A mechanism for changing an optical path of the measurement light adjusts a difference in optical path lengths of the optical path of the measurement light and the optical path of the reference light. For example, a distance between a collimator 112 and a galvano scanner 114 can be changed. Such a distance can be changed manually or electrically.

In the present example embodiment, a diameter of a light guide portion in an ejection end of the optical fiber end portion 111a is larger than an optical fiber core diameter. A mechanism that increases the diameter of the light guide portion to be larger than the optical fiber core diameter can be similar to that of the first example embodiment.

In the present example embodiment, an optical path length of the reference light is constant, and the reference light is not ejected to space. Therefore, a configuration of the optical path of the reference light can be simplified. Moreover, a coupling loss due to projection and reception of light and reflection by an end surface can be reduced. Moreover, since reflection from the optical fiber end portion 111a for projecting and receiving measurement light can be reduced, a coherence revival ghost due to the reflection from the optical fiber end portion 111a can be reduced.

The example embodiments have been described in detail. However, the present disclosure is not limited to the specific example embodiments, and various modifications and enhancements are possible without departing from the scope thereof. Although in each of the above example embodiments a Mach-Zehnder interferometer has been described as an example of an interferometer, the interferometer is not limited thereto. A Michelson interferometer can be used.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2016-091609, filed Apr. 28, 2016, which is hereby incorporated by reference herein in its entirety.

What is claimed is:

1. An ophthalmic imaging apparatus that captures a tomographic image of a subject's eye, the ophthalmic imaging apparatus comprising:
    a splitting unit configured to split light ejected from a wavelength-sweeping light source into a measurement light and a reference light;
    a detection unit configured to detect, as an interfering signal, a light obtained by combining a return light with the reference light, the return light being from the subject's eye when irradiated with the measurement light;
    a clock generating unit configured to generate a clock signal for sampling the detected interfering signal;
    an analog-to-digital converter configured to convert the detected interfering signal from an analog signal into a digital signal in accordance with the generated clock signal;
    a first optical fiber having at least one ejection end and disposed in an optical path of the reference light, the first optical fiber including a light guide portion for guiding the reference light within the first optical fiber; and
    a second optical fiber having at least one ejection end and disposed in an optical path of the measurement light, the second optical fiber including a light guide portion for guiding the measurement light within the second optical fiber,
    wherein the first optical fiber has such a structure that a diameter of the light guide portion inside the first optical fiber is gradually increased toward at least one ejection end of the first optical fiber, and
    wherein the second optical fiber has such a structure that a diameter of the light guide portion inside the second optical fiber is increased stepwise toward at least one ejection end of the second optical fiber.

2. The ophthalmic imaging apparatus according to claim 1, wherein the ejection end of the first optical fiber is oblique.

3. The ophthalmic imaging apparatus according to claim 1, further comprising a mechanism, as a Mach-Zehnder interferometer, configured to change an optical path length of the measurement light,
    wherein the second optical fiber is configured in such a manner that an optical path length of the reference light is constant, and
    wherein the diameter of the light guide portion of the ejection end of the first optical fiber is larger than a diameter of such light guide portion in a position different from a position of the ejection end of the first optical fiber.

4. The ophthalmic imaging apparatus according to claim 1,
    wherein an image capturable range of the ophthalmic imaging apparatus in a depth direction of the subject's eye is longer than a cavity length of the wavelength-sweeping light source.

5. The ophthalmic imaging apparatus according to claim 1, wherein the wavelength-sweeping light source is an external-cavity-type wavelength-sweeping light source.

6. The ophthalmic imaging apparatus according to claim 1,
    wherein the clock generating unit includes an interferometer including a first optical path and a second optical path having an optical path length difference with respect to the first optical path, the clock generating unit configured to generate, using one portion of the light ejected from the wavelength-sweeping light source, the clock signal for performing the sampling at a frequency corresponding to the optical path length difference, and
    wherein the tomographic image is obtained based on a digital signal obtained by performing the sampling.

7. The ophthalmic imaging apparatus according to claim 1, further comprising a trigger generating unit configured to generate a trigger signal, for recognizing a start and an end of every A-scan for the tomographic image, using one portion of the light ejected from the wavelength-sweeping light source.

8. The ophthalmic imaging apparatus according to claim 1, wherein the ophthalmic imaging apparatus has a signal-to-noise ratio that exceeds 90 dB.

9. The ophthalmic imaging apparatus according to claim 1,
    wherein the clock generating unit generates the clock signal using one portion of the light ejected from the wavelength-sweeping light source, and
    wherein the tomographic image is obtained based on a digital signal obtained by performing the sampling.

10. The ophthalmic imaging apparatus according to claim 1, wherein the light guide portion is a core.

11. An ophthalmic imaging apparatus that captures a tomographic image of a subject's eye, the ophthalmic imaging apparatus comprising:
    a splitting unit configured to split light ejected from a wavelength-sweeping light source into a measurement light and a reference light;
    a detection unit configured to detect, as an interfering signal, a light obtained by combining a return light with the reference light, the return light being from the subject's eye irradiated with the measurement light;
    a clock generating unit configured to generate a clock signal for sampling the detected interfering signal;
    an analog-to-digital converter configured to convert the detected interfering signal from an analog signal into a digital signal in accordance with the generated clock signal;
    a first optical fiber having at least one ejection end and disposed in an optical path of the reference light, the first optical fiber including a light guide portion for guiding the reference light within the first optical fiber; and a second optical fiber having at least one ejection end and disposed in an optical path of the measurement light, the second optical fiber including a light guide portion for guiding the measurement light within the second optical fiber, wherein at least one optical fiber of the first optical fiber and the second optical fiber has such a structure that a diameter of the light guide portion of said at least one optical fiber at at least one ejection end of said at least one optical fiber is larger than a diameter of the light guide portion at another position.

12. The ophthalmic imaging apparatus according to claim 11, wherein the ejection end of the first optical fiber and the ejection end of the second optical fiber are oblique.

13. The ophthalmic imaging apparatus according to claim 11, wherein the light guide portion of the first optical fiber and the light guide portion of the second optical fiber each include a first area and a second area, the first area having a first diameter in a position different from a position of the ejection end, and the second area having a second diameter larger than the first diameter in the ejection end.

14. The ophthalmic imaging apparatus according to claim 11, further comprising a Mach-Zehnder interferometer configured to change an optical path length of the measurement light, wherein the second optical fiber is configured in such a manner that an optical path length of the reference light is constant, and wherein the diameter of the light guide portion of the ejection end of the first optical fiber is larger than a diameter of the light guide portion in a position different from a position of the ejection end of the first optical fiber.

15. The ophthalmic imaging apparatus according to claim 11, wherein an image capturable range of the ophthalmic imaging apparatus in a depth direction of the subject's eye is longer than a cavity length of the wavelength-sweeping light source.

16. The ophthalmic imaging apparatus according to claim 11, wherein the wavelength-sweeping light source is an external-cavity-type wavelength-sweeping light source.

17. The ophthalmic imaging apparatus according to claim 11, wherein the clock generating unit includes an interferometer including a first optical path and a second optical path having an optical path length difference with respect to the first optical path, the clock generating unit configured to generate, using one portion of the light ejected from the wavelength-sweeping light source, the clock signal for performing the sampling at a frequency corresponding to the optical path length difference, and wherein the tomographic image is obtained based on a digital signal obtained by performing the sampling.

18. The ophthalmic imaging apparatus according to claim 11, wherein the clock generating unit generates the clock signal using one portion of the light ejected from the wavelength-sweeping light source, and wherein the tomographic image is obtained based on a digital signal obtained by performing the sampling.

19. The ophthalmic imaging apparatus according to claim 11, wherein the first optical fiber has such a structure that a diameter of the light guide portion of the first optical fiber is gradually increased toward at least one ejection end of the first optical fiber.

20. The ophthalmic imaging apparatus according to claim 11, wherein the second optical fiber has such a structure that a diameter of the light guide portion of the second optical fiber is increased stepwise toward at least one ejection end of the second optical fiber.

21. The ophthalmic imaging apparatus according to claim 11, wherein the light guide portion is a core.

22. An ophthalmic imaging apparatus that captures a tomographic image of a subject's eye, the ophthalmic imaging apparatus comprising:

a splitting unit configured to split light ejected from a wavelength-sweeping light source into a measurement light and a reference light;

a detection unit configured to detect, as an interfering signal, a light obtained by combining a return light with the reference light, the return light being from the subject's eye when irradiated with the measurement light;

a clock generating unit configured to generate a clock signal for sampling the detected interfering signal;

an analog-to-digital converter configured to convert the detected interfering signal from an analog signal into a digital signal in accordance with the generated clock signal;

a first optical fiber having at least one ejection end and disposed in an optical path of the reference light, the first optical fiber including a light guide portion for guiding the reference light within the first optical fiber; and a second optical fiber having at least one ejection end and disposed in an optical path of the measurement light, the second optical fiber including a light guide portion for guiding the measurement light within the second optical fiber, wherein at least one optical fiber of the first optical fiber and the second optical fiber has such a structure that a diameter of the light guide portion of said at least one optical fiber is increased toward at least one ejection end of said at least one optical fiber.

23. The ophthalmic imaging apparatus according to claim 22, wherein the first optical fiber has such a structure that a diameter of the light guide portion of the first optical fiber is gradually increased toward at least one ejection end of the first optical fiber.

24. The ophthalmic imaging apparatus according to claim 22, wherein the second optical fiber has such a structure that a diameter of the light guide portion of the second optical fiber is increased stepwise toward at least one ejection end of the second optical fiber.

25. The ophthalmic imaging apparatus according to claim 22, wherein the light guide portion is a core.

26. An ophthalmic imaging apparatus that captures a tomographic image of a subject's eye, the ophthalmic imaging apparatus comprising:

a splitting unit configured to split light ejected from a wavelength-sweeping light source into a measurement light and a reference light;

a detection unit configured to detect, as an interfering signal, a light obtained by combining a return light with the reference light, the return light being from the subject's eye irradiated with the measurement light;

a clock generating unit configured to generate a clock signal for sampling the detected interfering signal;

an analog-to-digital converter configured to convert the detected interfering signal from an analog signal into a digital signal in accordance with the generated clock signal;

a first optical fiber having at least one ejection end and disposed in an optical path of the reference light, the first optical fiber including a light guide portion for guiding the reference light within the first optical fiber; and a second optical fiber having at least one ejection end and disposed in an optical path of the measurement light, the second optical fiber including a light guide portion for guiding the measurement light within the second optical fiber, wherein a diameter of the light guide portion of at least one optical fiber of the first optical fiber and the second optical fiber is larger at at least one ejection end of said at least one optical fiber than away from said at least one ejection end.

27. The ophthalmic imaging apparatus according to claim 26, wherein the first optical fiber has such a structure that a diameter of the light guide portion of the first optical fiber is gradually increased toward at least one ejection end of the first optical fiber.

28. The ophthalmic imaging apparatus according to claim 26, wherein the second optical fiber has such a structure that a diameter of the light guide portion of the second optical fiber is increased stepwise toward at least one ejection end of the second optical fiber.

29. The ophthalmic imaging apparatus according to claim 26, wherein the light guide portion is a core.

* * * * *